United States Patent [19]

Demarcq

[11] 4,169,118

[45] Sep. 25, 1979

[54] PHOSPHORUS DERIVATIVES OF PENTAERYTHRITOL MONOBROMOHYDRIN

[75] Inventor: Michel Demarcq, Lyons, France

[73] Assignee: Produits Chimiques Ugine Kuhlmann, Paris, France

[21] Appl. No.: 803,769

[22] Filed: Jun. 6, 1977

Related U.S. Application Data

[62] Division of Ser. No. 703,582, Jul. 8, 1976, abandoned.

[30] Foreign Application Priority Data

Jul. 8, 1975 [FR] France ............................... 75 21320

[51] Int. Cl.$^2$ ............................................... C07F 9/40
[52] U.S. Cl. .................................. 260/927 R; 260/969
[58] Field of Search ........................... 260/927 R, 969

[56] References Cited

U.S. PATENT DOCUMENTS

| | | | |
|---|---|---|---|
| 3,033,887 | 5/1962 | Wadsworth et al. | 260/927 R |
| 3,257,355 | 6/1966 | Bean, Jr. | 260/927 X |
| 3,922,323 | 11/1975 | Reese et al. | 260/927 R |
| 3,978,166 | 8/1976 | Hechenbleikner | 260/937 X |

OTHER PUBLICATIONS

Verkade, "Coordination Chemistry Reviews," vol. 9 (1972/73), pp. 3& 9.
Milbrath et al., "J.A.C.S.", vol. 98(18), p. 5493, (1976).

*Primary Examiner*—Anton H. Sutto
*Attorney, Agent, or Firm*—Brooks, Haidt, Haffner & Delahunty

[57] ABSTRACT

Novel bicyclic phosphorus derivatives of 2,2-di(hydroxymethyl)-3-bromopropanol having the formula

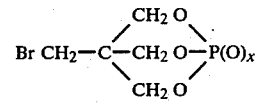

where x is zero or one, novel polyphosphonate derivatives of the phosphite derivatives obtained by Michaelis-Arbuzov condensation and other processes; and processes for preparing such novel compounds, the bicyclic derivatives being useful as plastic stabilizers, fireproofing agents and intermediates and the polyphosphonates being useful as fireproofing agents for polymers and textiles.

5 Claims, No Drawings

PHOSPHORUS DERIVATIVES OF PENTAERYTHRITOL MONOBROMOHYDRIN

This is a divisional of Ser. No. 703,582 filed July 8, 1976 now abandoned.

BACKGROUND OF THE INVENTION

The present invention relates to the bicyclic phosphite of pentaerythritol monobromohydrin and processes for producing same, and additionally, it relates to the corresponding bicyclic phosphate and to a new family of polyphosphonates produced therefrom, and process for making and using same.

Certain bicyclic esters of phosphorous acid (Formula I) and of phosphoric acid (Formula II) having the bicyclo [2.2.2] octane structure are known:

$$Z-C(CH_2-O)_3P \quad (I) \qquad Z-C(CH_2-O)_3PO \quad (II)$$

The first phosphites and phosphates of types I and II (with Z being $CH_3$, $C_2H_5$, higher alkyls, or $HOCH_2$) seem to have been prepared initially by chemists at Hooker Chemical Corporation (British Pat. No. 889,338, published Feb. 14, 1962, claiming a U.S. priority date of July 21, 1958), but the first publication relating to these compounds was J. G. Verkade and L. T. Reynolds, *J. Org. Chem.* 25, 663 (1960) with the synthesis of phosphite (I) with Z being $CH_3$.

Other similar phosphites where Z was $C_2H_5$, $HOCH_2$, $CH_3COOCH_2$, $CH_2=CH(CH_3)COOCH_2$, and $CH_3(CH_2)_3CH(C_2H_5)COOCH_2$ were prepared by O. Neunhoffer and W. Maiwald, *Chem. Ber.* 95, 108 (1962) and by W. S. Wadsworth, Jr. and W. D. Emmons, *J.A.C.S.* 84, 610 (1962). The latter workers also described phosphates (II) where Z was $C_2H_5$ and $CH_2=CH(CH_3)COOCH_2$.

Phosphite (I) and the corresponding phosphate (II) with Z being H have only been prepared more recently by E. J. Boros et al, *J.A.C.S.* 88, 1140 (1966).

Phosphate (II) with Z being $NO_2$ was prepared in 1926 by F. Zetzsche and E. Zurbrugg, *Helv. Chim. Acta* 9, 298 (1926). Its synthesis was repeated by W. H. Chang, *J. Org. Chem.* 29, 3711 (1964), and he at the same time also showed phosphates (II) with Z as $C_6H_5$ and $C_6Cl_5-OCH_2$. Last, G. Kamai and E. T. Mukmenev, *Zh. Obschei Khim.*, 33, 3197 (1963) have reported the preparation of a diphosphite corresponding to Formula (I) where Z is $(C_2H_5O)_2POCH_2$.

THE INVENTION

The present invention relates to the discovery of new bicyclic phosphites and phosphates of pentaerythritol monohalohydrin, to new polyphosphonates, to the processes for producing such novel products, and to processes for utilizing the novel products.

The first class of novel products produced according to the present invention are bicyclic pentaerythritol monobromohydrin derivatives having the inclusive structural formula $$Br\,CH_2-C(CH_2-O)_3P(O)_x \quad (III)$$

where x is an integer which is 0 or 1.

The present invention further relates to polyphosphonates having the generic formula:

$$(G)_y E(A)_{n-1}(X)_{n-p+y}(PO_3R_2)_p \quad (IV)$$

wherein G is a radical selected from the group consisting of hydrogen, halogen, the $$OP(OCH_2)_3C-CH_2-\text{ radical},$$

mono- and polyvalent hydrocarbon radicals, the $$CYY'=CH-O-\text{ radical}$$

where Y and Y' are the same or different and are hydrogen, chlorine, bromine, or alkyl groups;

A is $$-P(=O)(OCH_2)_2C(CH_2-)_2$$

B is $$P(OCH_2)_3C-CH_2-$$

E is A when y is one and can be A or B when y is zero;

X represents the same or different atoms selected from the group consisting of bromine, chlorine, and iodine, one at the most of them being chlorine or iodine when y is 1 and all being bromine when y is zero;

R is an aliphatic radical containing from one to about 20 carbon atoms;

y is zero or one;

n is an integer from one to 500; and p is an integer from zero to n+y.

The present invention has made it possible to succeed in the preparation of the crystalline form of the phosphite of Formula I where Z is $BrCH_2$ (that is, Formula III where x is zero). This result was completely unforeseen with such a phosphite having a very reactive halomethyl group in its molecule and a tertiary phosphite grouping, this latter also being very reactive. Prior to the present work, it was considered that the material was so liable to auto-condensation that it could not be obtained in the pure form.

The present invention has equally succeeded in preparing the bicyclic phosphate of Formula II wherein Z is $BrCH_2$ (Formula III wherein x is one) by oxidation of phosphite III where x is zero.

The phosphite of Formula III where x is zero can be obtained by reaction of phosphorus trichloride with pentaerythritol monobromohydrin according to the equation $$PCl_3 + (HOCH_2)_3C-CH_2Br \rightarrow (III) + 3HCl$$

This reaction can be carried out at a temperature of from −40° to 100° C. It is desirably conducted in the presence of one or more inert vehicles. Suitably inert vehicles include aliphatic hydrocarbons such as hexane, heptane, and the like; aromatic and alkaryl hydrocarbons such as benzene, toluene, xylene, cumene, and the like; halogenated aliphatic and aromatic hydrocarbons such as chloroform, chlorobenzene, and the like; ethers (including internal ethers) such as diethyl ether, tetrahydrofuran, dioxane, and the like.

A tertiary amine can be used, if desired, in certain embodiments of the invention to neutralize the hydrogen chloride formed in the reaction. Thus, in certain embodiments, aliphatic and cyclic amines such as triethylamine, pyridine, alpha-picoline, dimethylaniline, diethylaniline, N-methylmorpholine, and the like can be used.

The phosphite of Formula III with x being zero can also be prepared by transesterification of a trialkyl phosphite or a triaryl phosphite of the pentaerythritol monobromohydrin, alone or in the presence of a basic catalyst. Suitable basic catalysts include the alkali metal and alkaline earth metal hydroxides, alcoholates, phenates, hydrides, amides, carbonates, or acid carbonates; aluminum alcoholates; or tertiary amines. The reaction, in this case, can advantageously be carried out under a pressure of from 0.5 to 50 mm Hg and a temperature from about 20° to 120° C.

It should be understood that the stability of phosphite (III) when x is zero is limited. Initially phosphite (III) is entirely soluble in benzene, but after a few days' storage at room temperature protected from moisture, it is no more than partially soluble. It is accordingly desirable to keep it under refrigeration or to use it immediately following its preparation.

The oxidation of phosphite (III) of this invention to the novel phosphate (III) where x is one can be carried out by means of a number of oxidizing agents. These include concentrated hydrogen peroxide, organic peroxides, ozone, nitrogen oxides, mixtures of oxygen and nitrogen oxides, and alkali metal permanganates. It has been found desirable to carry out such oxidation in the presence of one or more inert vehicles. Such inert oxidation vehicles include aliphatic hydrocarbons such as hexane, heptane, and the like; aromatic and alkaryl hydrocarbons such as benzene, toluene, xylene, cumene, and the like; halogenated aliphatic and aromatic hydrocarbons such as chlorobenzene, chloroform, tetrachloromethane, and the like; ethers such as diethyl ether and the like; nitriles such as acetonitrile and the like; and esters such as ethyl acetate and the like.

Phosphate (III) where x is one can also be obtained by the direct reaction of phosphorus oxychloride with pentaerythritol monobromohydrin.

The products of Formula IV wherein y and p are zero and X is bromine are obtained by polycondensation of phosphite III with x being zero. Such polycondensation is carried out according to the present invention by simple heating of the aforesaid phosphite at a temperature of from 80° to 250° C. The polycondensation is in certain embodiments desirably carried out in a heavy inert polycondensation vehicle. Such polycondensation vehicles include alkyl aromatic hydrocarbons such as xylene, cumene, and the like; hydrogenated polynuclear aromatic hydrocarbons such as tetralin and the like; and chlorinated aromatic hydrocarbons such as chlorobenzene, orthodichlorobenzene, various trichlorobenzenes, chloronaphthalenes, and the like.

In cases where the reaction is not forced as far as total disappearance of the tricoordinate phosphorus, it proceeds according to the equation:

$$N[III(x \neq 0)] \rightarrow B(A)_{n-1}(Br)_n$$

wherein A, B, and n have the meaning given above. The polyphosphonate obtained according to the present invention will have in this instance an open "tree" structure (Type "O") such as represented by the following formula:

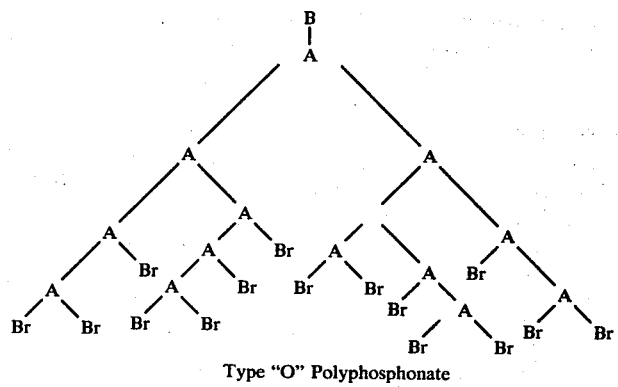

Type "O" Polyphosphonate

When the reaction is forced to the total disappearance of tricoordinate phosphorus, it follows the equation:

$$n[III(x=0)] \rightarrow (A)_n(Br)_n$$

where A and n have the meaning stated above. In this case the polyphosphonate obtained will generally have a higher molecular weight than in the case of the Type "O" polyphosphonate and it will be "closed" or Type "F". In other words, it will involve a supplementary branch-root junction, as illustrated in the following structure:

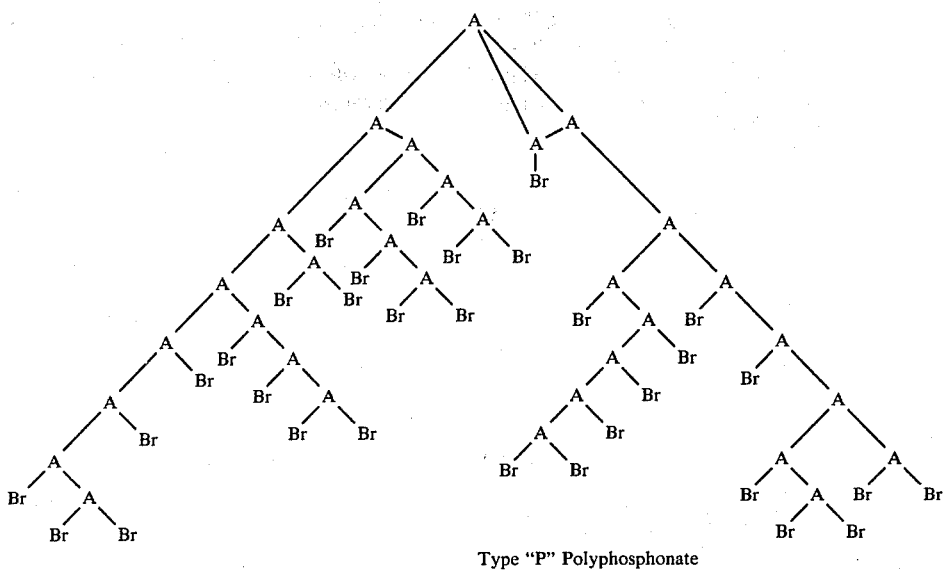

Type "P" Polyphosphonate

The mixed polyphosphonates of Formula IV in which y is one, p is zero, E is A, and G is hydrogen, halogen, or mono- or polyvalent hydrocarbon radicals, are obtained by heating phosphite (III) where x is zero, or its Type "O" prepolymers with a halogenide GX, wherein X is chlorine, bromine, or iodine. Halogenide GX can be any of the known halogenides which give with trialkyl phosphites the Michaelis-Arbuzov reaction leading to a phosphonate. This reaction can be written:

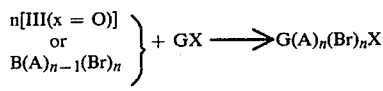

The polyphosphonate obtained will in this case itself also have an open "tree" structure which can be derived from Type "O" polymer by simply replacing B by G.

The halogenide GX can also be the type of halogenides which give with trialkyl phosphites the so-called Perkow reaction leading to a vinylic phosphate. In this case, the polymer obtained is still also able to be shown by the Type "O" structure above, modified by replacing B with a CYY′=CH—O— radical, Y and Y′ having the meaning set forth above.

As instances of the halogenide GX desirably used according to the processes of the present invention, there are chlorine; bromine; iodine; hydrogen chlorides, bromides, and iodides; the chlorides, bromides, and iodides of alkyls such as methyl, ethyl, propyl, butyl, allyl, and the like; chlorides, bromides, and iodides of aryl alkyls such as benzyl and xylylene and the like or of carbonyl compounds such as acetyl, acryloyl, methacryloyl, and the like; methylchloromethyl ether, chloroformic and chloracetic esters, chloral, or phosphate (III) with x being 1.

Mixed polyphosphonates of Formula IV wherein p is not zero of the second type can also be prepared by heating together phosphite (III) where x is zero or one of its Type "O" or "F" prepolymers with another trialiphatic phosphite $(RO)_3P$ where R is an aliphatic group containing from one to 20 carbon atoms. The polyphosphonate structure obtained can be derived from those of Types "O" and "F" by replacing all or part of the bromine atoms by the $-PO(OR)_2$ radical.

The overall reaction can then be written:

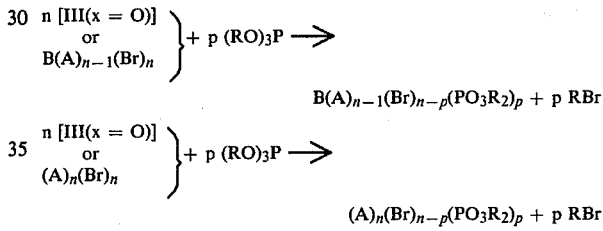

where A, B, n and p have the same meaning set forth above.

Phosphite (III) where x is zero has utility as a stabilizer for plastics and as an intermediate for producing insecticides. Phosphate (III) where x is one is useful as a fire-retardant for plastics and synthetic fibers and as an intermediate for the preparation of esters with phosphoric functional groups.

Because of the high phosphorus and bromine content and because of their highly branched structure, the polyphosphonate derivatives of the phosphite (III) find numerous uses. For instance, they can be used as fire-retardant additives with a low migration rate in vinyl and acrylic polymers and in synthetic textiles.

All parts, percentages, proportions and ratios herein are by weight, unless otherwise stated.

The following examples are given to illustrate embodiments of the invention as it is presently preferred to practice it. It will be understood that these examples are illustrative, and the invention is not to be considered as restricted thereto except as indicated in the appended claims.

EXAMPLE I

Preparation of Bicyclic Phosphite of 2,2-di(Hydroxymethyl)-3-bromopropanol

A flask fitted with a thermometer, dip tube, low-speed mechanical agitator and a reflux condenser cooled with dry ice, is charged with 0.1 mol of phosphorus trichloride and 0.1 mol of pentaerythritol monobromohydrin. During the reaction, agitation is provided by the agitator as well as by gentle bubbling of dry nitrogen. Under the influence of the removal of hydrogen chloride formed, the temperature first falls from 20° to 0° C. and then slowly rises to its initial value.

After about five hours, the mixture is diluted with 25 ml of hexane and 12 ml of benzene. It is thereafter heated for two hours at 40° C. and then for one hour at 60° C. with continuous nitrogen bubbling. Upon cooling, crystals appear and these are rapidly dried on a fritted glass filter and washed with a 1:1 hexane:benzene mixture. After drying under vacuum, 22 g of crude colorless hygroscopic crystals are obtained, for a yield of 97 percent.

A further crystallization from a mixture of 25 percent hexane and 75 percent benzene provides purified crystals sharply melting at 88° C. and containing 12.96 percent P (calculated: 13.67 percent) and 34.10 percent Br (calculated: 35.2 percent). The proton magnetic resonance spectrum of the phosphite dissolved in deuterochloroform shows a doublet, J=2 Hz at 4.03 ppm (part per million) attributable to $POCH_2$ groups and a peak at 3.00 ppm, attributable to the $CH_2Br$ group, in the theoretical intensity ratio of 6/2, the chemical displacements being reckoned by reference to hexamethyldisiloxane as the internal standard. The $^{31}P$ nuclear magnetic resonance spectrum of the phosphite dissolved in deuteroacetone shows a sextuplet J=2 Hz centered at 92.1 ppm downfield from 85% $H_3PO_4$ as the external standard.

EXAMPLE II

Preparation of Bicyclic Phosphate of 2,2-di(Hydroxymethyl)-3-bromopropanol

A solution of 20 g of freshly prepared phosphite, as obtained in Example I, in 500 ml of a 1:1 hexane:benzene mixture is agitated vigorously at room temperature under an atmosphere comprised of oxygen and nitrogen tetroxide, $N_2O_4$. A precipitate forms rapidly, is collected on a filter, washed with hexane, and dried under vacuum.

The product is 21.2 g of colorless crystals melting at 161°-162° C. and containing 13.4 percent P (calculated: 12.8 percent) and 33.2 percent Br (calculated: 32.9 percent).

EXAMPLE III

Preparation of a Polyphosphonate

A 25 g portion of the phosphite prepared according to the process of Example I is heated by means of a metal bath in a glass cylinder fitted with a piston. The piston progressively pushes into the cylinder in the course of the condensation, because this is accompanied by a contraction of the material. The temperature is raised from 150° to 200° C. during the course of five hours and is then maintained at the higher temperature for seven hours.

A colorless, translucent glassy polymer is obtained which is hard at ambient temperature and which softens at about 200° C.

EXAMPLE IV

Preparation of Phosphate-Polyphosphonate

Following the procedure of Example III, 2.5 g of the phosphate of Example II and 22.5 g of the phosphite of Example I are heated together for five hours at 160°-190° C., and they are then heated for nine hours at 200° C.

The product is a colorless glassy polymer which is hard at room temperature.

EXAMPLE V

Preparation of Mixed Polyphosphonate

Following the process of Example III, one gram of p-xylylene dichloride is heated with 24 g of the phosphite produced in Example I for three hours at 130°-200° C. The mixture is then maintained at 200° C. for eight hours.

The product is a pale yellow vitreous polymer which is hard at room temperature.

EXAMPLE VI

Preparation of Phosphate-Polyphosphonate

Following the procedure of Example III, one gram of freshly redistilled anhydrous chloral is heated with 24 g of the phosphite produced in Example I for two hours at 90°-150° C. The heating is then continued for two hours at 150°-180° C. and thereafter for seven hours at 180°-190° C.

The product is a vitreous polymer which is hard at room temperature.

EXAMPLE VII

Preparation of Mixed Polyphosphonate

Following the procedure of Example III, 5 g of triethyl phosphite and 20 g of the phosphite produced in Example I are heated together for six hours at 150°-190° C.

The product is a colorless polymer which remains soft at room temperature.

EXAMPLE VIII

Bicyclic Phosphate of 2,2-di(hydroxymethyl)-3-bromopropanol 6 g of phosphite of Example I and 4 g of cumene hydroperoxide in 100 ml of a 1:1 hexane:benzene mixture are let to stand at room temperature. The precipitate formed after one hour is collected on a filter, washed with hexane and dried. It melts at 163° C. The $^1H$ n.m.r spectrum (in $CDCl_3$) shows a doublet J≃6,6 Hz at 4.60 ppm ($POCH_2$) and a singlet at 3.42 ppm ($CH_2Br$) from hexamethyldisiloxane; intensity ratio=6/2. The $^{31}P$ n.m.r spectrum (in $CD_3COCD_3$) shows a septuplet J=6.6 Hz centered at 8.7 ppm upfield from 85% $H_3PO_4$.

EXAMPLE IX

Preparation of a Polyphosphonate

A solution of 25 g of phosphite of Example I in 25 g orthodichlorobenzene is heated for 10 hours at 180° C. A glass separates as a colorless, transparent, heavy layer. This is redissolved in DMF-acetone and precipitated by hexane, yielding a purified polymer.

It will be apparent to those skilled in the art from the present disclosure that a variety of polyphosphonates and mixed polyphosphonates can be obtained according to the present invention.

What is claimed is:

1. Branched polyphosphonates having the formula $(G)_yE(A)_{n-1}(X)_{n-p+y}(PO_3R_2)_p$, wherein G is a radical which is hydrogen, a halogen, a

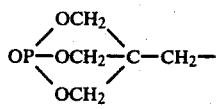

group, a monovalent hydrocarbon group, xylylene, or a CYY'=CH—O— group, and where

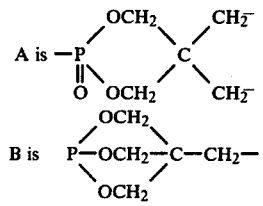

E is A, when y is one, and B, when y is zero;
X is the same or different and is bromine, chlorine, or iodine, at the most one being chlorine or iodine when y is one and all being bromine when y is zero;
R is an aliphatic radical having from one to 20 carbon atoms;
Y and Y' are hydrogen, chlorine, bromine, or an alkyl group;
y is zero or one;
n is an integer from two to 500; and
p is an integer from zero to n+y, the alkyl groups containing from one to four carbon atoms.

2. A process for preparing polyphosphonates according to claim 1 where y and p are zero and X is bromine, which process comprises carrying out a Michaelis-Arbuzov autopolycondensation of

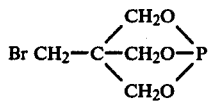

at a temperature of 80° to 250° C.

3. A process for preparing polyphosphonates according to claim 1 where y is one, p is zero, E is A, and G is hydrogen, halogen, or mono- or polyvalent hydrocarbon radicals, which process comprises carrying out a Michaelis-Arbuzov reaction of

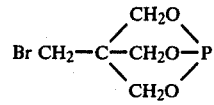

or a polyphosphonate according to the formula $E(A)_{n-1}(Br)_n$ with halogenide having the formula GX, where X is chlorine, bromine, or iodine; G is hydrogen, X, or a mono- or polyvalent hydrocarbon group; and E, A, and n have the meaning set forth in claim 1.

4. A process for the preparation of polyphosphonates according to claim 1 where G is CYY'=CH—O—, which process comprises condensing

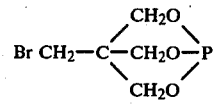

or a polyphosphonate according to the formula $E(A)_{n-1}(Br)_n$ with a halogenide having the formula X-CYY'=CH—O, E, A, X, Y, Y', and n having the meaning set forth in claim 1.

5. A process for preparing the compounds of claim 1 wherein p is non-zero, which process comprises heating

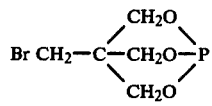

or a polyphosphonate having the formula $(G)_y E\text{-}(A)_{n-1}(X)_{n+y}$ with a trialiphatic phosphite $P(OR)_3$ wherein R is an aliphatic group containing from one to 20 carbon atoms and G, E, A, X, n and y have the meaning set forth in claim 1.

* * * * *